United States Patent [19]

Hörold

[11] Patent Number: 5,854,371

[45] Date of Patent: Dec. 29, 1998

[54] PHOSPHORUS-MODIFIED EPOXY RESIN MIXTURES COMPRISING EPOXY RESINS, PHOSPHORUS-CONTAINING COMPOUNDS AND A CURING AGENT

[75] Inventor: Sebastian Hörold, Erftstadt, Germany

[73] Assignee: Hoechst Aktiengesellschaft, Frankfurt, Germany

[21] Appl. No.: 824,641

[22] Filed: Mar. 27, 1997

[30] Foreign Application Priority Data

Apr. 1, 1996 [DE] Germany ......................... 196 13 065.4
Mar. 10, 1997 [DE] Germany ......................... 197 09 519.4

[51] Int. Cl.$^6$ ......................... C08G 59/14; C08G 59/30; C08G 59/40; C09K 21/14
[52] U.S. Cl. ......................... 528/108; 528/398; 528/400; 428/413; 428/901; 525/327.3; 525/507
[58] Field of Search ......................... 528/108, 398, 528/400; 428/413, 901; 525/327.3, 507

[56] References Cited

U.S. PATENT DOCUMENTS

| | | | |
|---|---|---|---|
| 3,334,110 | 8/1967 | Schramm | 260/307 |
| 3,378,526 | 4/1968 | Vogt et al. | 528/108 |
| 3,477,982 | 11/1969 | Dijkstra et al. | 260/37 |
| 4,138,433 | 2/1979 | Kleiner et al. | 260/545 P |
| 4,289,812 | 9/1981 | Martin | 427/379 |
| 5,364,893 | 11/1994 | von Gentzkow et al. | 523/429 |

FOREIGN PATENT DOCUMENTS

| | | |
|---|---|---|
| 2158361 | 9/1994 | Canada . |
| 384939 | 9/1990 | European Pat. Off. . |
| 1745796 | 3/1972 | Germany . |
| 2528420 | 1/1977 | Germany . |
| 2652007 | 5/1978 | Germany ................ 528/108 |
| 2652052 | 5/1978 | Germany ................ 528/108 |
| 2757733 | 7/1978 | Germany . |
| 3540524 | 5/1987 | Germany . |
| 4308185 | 9/1994 | Germany . |

OTHER PUBLICATIONS

*Lackkunstharze* [Synthetic Paint Resins]Wagner/Sarx, 5th ed., Carl Hanser Verlag (1971), pp. 174–194.

Bald, G., et l, *Angewandte Makromol. Chem. 44* : 151–163 (1975).

Chemical Abstracts, vol. 108, No. 18, "Flame Retardant Polyester–Epoxy Adhesive Compositions".

*Primary Examiner*—Frederick Krass
*Attorney, Agent, or Firm*—Miles B. Dearth

[57] ABSTRACT

The invention relates to a flame-resistant epoxy resin mixture comprising epoxy resins, phosphorus-containing compounds and a curing agent, wherein the epoxy resin mixture comprises phosphorus-containing structural units of the formula I

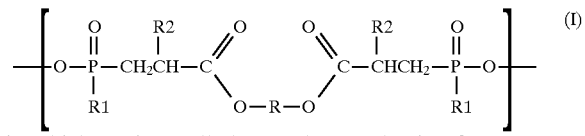

in which R1 is an alkyl or aryl group having from 1 to 10 carbon atoms, R2 is hydrogen or an alkyl group having from 1 to 4 carbon atoms and R is an alkylene, cycloalkylene or arylene group having from 2 to 20 carbon atoms.

3 Claims, No Drawings

PHOSPHORUS-MODIFIED EPOXY RESIN MIXTURES COMPRISING EPOXY RESINS, PHOSPHORUS-CONTAINING COMPOUNDS AND A CURING AGENT

The present invention relates to phosphorus-modified epoxy resin mixtures comprising epoxy resins, phosphorus-containing compounds and a curing agent, to a process for their preparation and to their use. These epoxy resin mixtures are distinguished by their flame resistance.

Epoxy resins are currently employed in the production of molding compounds and coatings having high-grade thermal, mechanical and electronic properties. They are suitable for encapsulating electrical and electronic components and for impregnation processes. The large majority of epoxy resin molding compositions used in the electrical industry are flame-resistant.

Epoxy resin molding compositions are generally made flame-resistant using bromine-containing aromatic compounds, in particular tetrabromobisphenol A. If only brominated flame retardants are employed, a bromine content of about 20% is needed to ensure that the molding compositions are self-extinguishing. Antimony trioxide is frequently used as synergist. In a fire, hydrogen bromide is liberated and can cause damage through corrosion. Under unfavorable conditions, polybrominated dibenzodioxins and furans may also be formed. There is therefore a need for epoxy resin molding compositions which achieve the required flame resistance without the addition of brominated compounds.

Furthermore, it is necessary to ensure that no ecologically or toxicologically questionable products can be produced on decomposition under the influence of heat.

Filler materials which have an extinguishing effect, such as alumina trihydrate, have already been proposed as flame retardants for epoxy resin molding compositions (DE 35 40 524 Al). Adequate flame resistance can also be achieved by the addition of ammonium polyphosphate, if desired in combination with alumina trihydrate. In place of ammonium polyphosphate, red phosphorus can also be used (DE 17 45 796 Al).

A disadvantage with all the flame retardants which are fillers is that the transparency of the materials is not retained. A great many liquid organophosphorus compounds have been proposed as flame-retardant additives for plastics. A disadvantage of these systems, however, is the marked "plasticizer effect" of the additives. In cured epoxy resins, the plasticizing effect is evident from a severe reduction in the glass transition temperature.

Phosphorus-modified epoxy resins obtained by reaction of polyepoxide compounds with anhydrides of phosphonic acids or phosphinic acids and distinguished by good flame-resistant properties are known from the literature (DE 43 08 185 Al).

The use of epoxide-functional phosphonic acid esters to confer flame-resistant properties on epoxy resins has been described (EP 0 384 939 Al). A disadvantage of these systems is the high complexity of the synthesis of such phosphonic acid esters.

There is therefore a considerable need for flame-resistant (coating) materials which are based on epoxy resins and which have high flame resistance, but which do not contain halogen-containing constituents or other ecologically or toxicologically questionable substances or liberate such substances on decomposition under the influence of heat.

The object of the invention was therefore to provide flame-resistant (coating) materials having the above-mentioned properties. Furthermore, they should be easy to produce and to use.

The invention therefore relates to a flame-resistant epoxy resin mixture comprising epoxy resins, phosphorus-containing compounds and a curing agent, wherein the epoxy resin mixture comprises phosphorus-containing structural units of the formula I

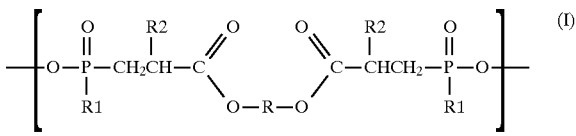

in which R1 is an alkyl or aryl group having from 1 to 10 carbon atoms, R2 is hydrogen or an alkyl group having from 1 to 4 carbon atoms and R is an alkylene, cycloalkylene or arylene group having from 2 to 20 carbon atoms.

The flame-resistant epoxy resin mixture preferably contains from 10 to 100 parts by weight of phosphorus-containing compounds of the formula I per 100 parts by weight of epoxy resin, the total weight ratio of epoxy resin and phosphorus-containing compound of formula I to curing agent being from 1:1 to 10:1.

The flame-resistant epoxy resin mixture is preferably halogen-free.

The flame-resistant epoxy resin mixture preferably includes from 5 to 300 parts by weight of phosphorus-free epoxy resins.

The flame-resistant epoxy resin mixture preferably includes from 5 to 300 parts by weight of other ingredients and/or fillers.

The flame-resistant epoxy resin mixture preferably includes from 0.5 to 13% by weight of phosphorus, based on the total weight of the flame-resistant epoxy resin mixture.

The flame-resistant epoxy resin mixture particularly preferably includes from 1 to 6% by weight of phosphorus, based on the total weight of the flame-resistant epoxy resin mixture.

The flame-resistant epoxy resin mixture preferably includes an accelerator.

The object of the invention is likewise achieved by a process for preparing flame-resistant epoxy resin mixtures comprising epoxy resins, phosphorus-containing compounds and a curing agent, which comprises a) in a first reaction step, heating a polyepoxide compound having at least 2 epoxide groups per molecule together with a 2,5-dioxo-1,2-oxaphospholane of the formula II

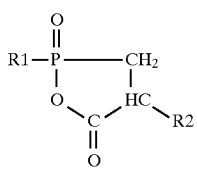

where R1 and R2 are as defined in formula I, until a homogeneous melt is produced, and b) in a second reaction step, adding a diol of the formula HO—R—OH, where R is as defined in formula I, to the melt, and c) in a third reaction step, forming from the 2,5-dioxo-1, 2-oxaphospholane in the homogeneous melt and the added diol HO—R—OH a diphosphinic acid of the formula III, which reacts directly with the polyepoxide compound.

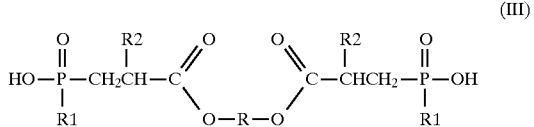

(III)

In an alternative embodiment, the process comprises
a) in a first reaction step, reacting a 2,5-dioxo-1,2-oxaphospholane of the formula II with a diol of the formula HO—R—OH, where R is as defined in formula I, giving a diphosphinic acid of the formula III, and then
b) in a second reaction step, reacting the diphosphinic acid with a polyepoxide compound having at least two epoxide groups per molecule.

The reactions are preferably carried out in a solvent. The aprotic, polar solvents employed are preferably N-methylpyrrolidone, dimethylformamide, tetrahydrofuran, dioxane, dialkyl ethers, glycol ethers, ketones and/or esters.

Likewise suitable are ethylene glycol ethers, propylene glycol ethers and butylene glycol ethers of monoalcohols having unbranched or branched alkyl radicals with from 1 to 6 carbon atoms, and ketones, such as acetone, methyl ethyl ketone, methyl isopropyl ketone, methyl isobutyl ketone, cyclohexanone and the like, but also esters, such as ethyl acetate, butyl acetate, ethylene glycol acetate and methoxypropyl acetate.

Preferred solvents are likewise halogenated hydrocarbons and aliphatic, cycloaliphatic and/or aromatic hydrocarbons, individually or as mixtures. Of these preference is given to hexane, heptane, cyclohexane, toluene and bixylenes.

The reactions are preferably carried out at temperatures between −10° and +200° C.

The reactions are particularly preferably carried out at temperatures from 70° to 130° C.

In the first reaction step of one of the novel processes, a polyepoxide compound having at least two epoxide groups per molecule and a 2,5-dioxo-1,2-oxaphospholane of the formula II

(II)

where R1 and R2 are as defined in formula I are precharged and heated until a homogeneous melt is formed. A diol of the formula HO—R—OH, where R is as defined in formula I, is then added dropwise.

Alternatively, the diol can also be added directly (process variant). A diphosphinic acid of formula III is formed from the diol and the 2,5-dioxo-1,2-oxaphospholane, and reacts directly with the epoxy resin.

The diol HO—R—OH can be, for example, ethylene glycol, propanediol, butanediol, cyclohexanediol, resorcinol or hydroquinone.

The 2,5-dioxo-1,2-oxaphospholane of formula II can, as described in DE 25 28 420 Al, be prepared from dihalophosphines and an unsaturated carboxylic acid, followed by elimination of chlorine, for example using water or acetic acid.

The halogen-free epoxide compounds employed according to the invention (also referred to as polyepoxide compounds) can be saturated or unsaturated and aliphatic, cycloaliphatic, aromatic and/or heterocyclic. They can also contain substituents which do not give rise to unwanted side-reactions under the conditions of mixing or of reaction, for example alkyl or aryl substituents, ether groups or the like. Mixtures of different polyepoxide compounds can also be used. The mean molecular weight $M_n$ of these polyepoxide compounds can be up to about 9000, but is generally from about 150 to 4000.

These polyepoxide compounds are, for example, polyglycidyl ethers based on polyhydric, preferably dihydric, alcohols, phenols, or hydrogenation products of these phenols, and/or based on novolaks (reaction products of mono- or polyhydric phenols, such as phenol and/or cresols, with aldehydes, in particular formaldehyde, in the presence of acid catalysts), obtained in a known manner, for example by reaction of the appropriate polyols with epichlorohydrin.

Polyhydric phenols which which may be mentioned by way of example are: resorcinol, hydroquinone, 2,2-bis(4-hydroxyphenyl)propane (bisphenol A), isomer mixtures of dihydroxydiphenylmethane (bisphenol F), 4,4'-dihydroxydiphenylcyclohexane, 4,4'-dihydroxy-3,3'-dimethyldiphenylpropane, 4,4'-dihydroxydiphenyl, 4,4'-dihydroxybenzophenone, 1,1-bis(4-hydroxyphenyl)ethane, 1,1'-bis(4-hydroxyphenyl)-isobutane, 2,2-bis(4-hydroxy-tert-butylphenyl)propane, bis(2-hydroxynaphthyl)methane, 1,5-dihydroxynaphthalene, tris(4-hydroxyphenyl)methane, bis(4-hydroxyphenyl) ether. Bisphenol A and bisphenol F are preferred.

The polyglycidyl ethers of polyhydric aliphatic alcohols are also suitable as polyepoxide compound. 1,4-Butanediol, 1,6-hexanediol, polyalkyleneglycols, glycerol, trimethylolpropane, 2,2-bis(4-hydroxycyclohexyl)propane and pentaerythritol may be mentioned as examples of such polyhydric alcohols.

Other suitable polyepoxide compounds are (poly)glycidyl esters, obtainable by reaction of epichlorohydrin or similar epoxy compounds with an aliphatic, cycloaliphatic or aromatic polycarboxylic acid, such as oxalic acid, adipic acid, glutaric acid, phthalic, isophthalic, terephthalic, tetrahydrophthalic or hexahydrophthalic acid, 2,6-naphthalenedicarboxylic acid or dimerized fatty acids. Examples are diglycidyl terephthalate and diglycidyl hexahydrophthalate.

Polyepoxide compounds which have epoxide groups randomly distributed over the molecular chain and are prepared by emulsion copolymerization using olefinically unsaturated compounds which contain these epoxide groups, such as, for example, glycidyl esters of acrylic or methacrylic acid, can advantageously be employed in some cases.

Other polyepoxide compounds which can be used are those based on heterocyclic ring systems, such as, for example, hydantoin epoxy resins, triglycidyl isocyanurate and/or its oligomers, triglycidyl-p-aminophenol, triglycidyl-p-aminodiphenyl ether, tetraglycidyldiaminodiphenylmethane, tetraglycidyldiaminodiphenyl ether, tetrakis(4-glycidoxy-phenyl)ethane, urazole epoxides, uracil epoxides and oxazolidinone-modified epoxy resins; also polyepoxides based on aromatic amines such as aniline, for example N,N-diglycidylaniline, or based on diaminodiphenylmethane or N,N'-dimethylaminodiphenylmethane or -sulfone.

Other suitable polyepoxide compounds are described in the "Handbook of Epoxy Resins" by Henry Lee and Kris Neville, McGraw-Hill Book Company, 1967, in the monograph by Henry Lee "Epoxy Resins", American Chemical Society, 1970, in Wagner/Sarx, "Lackkunstharze" [Synthetic Paint Resins], Carl Hanser Verlag (1971), 5th Edition, p. 174 ff., in "Angew. Makromol. Chemie" Vol. 44 (1975), pp. 151–163, in DE 27 57 733 Al and in EP 0 384 939 Al, which are incorporated herein by way of reference.

Preferred polyepoxide compounds are bisglycidyl ethers based on bisphenol A, bisphenol F or bisphenol S, reaction products of these bisphenols with epichloro(halo)-hydrin or oligomers of these, polyglycidyl ethers of phenol-formaldehyde and/or cresol-formaldehyde novolaks or diglycidyl esters of phthalic, isophthalic, terephthalic, tetrahydrophthalic and/or hexahydrophthalic acid or of trimellitic acid, N-glycidyl compounds of aromatic amines or of heterocyclic nitrogenous bases, such as N,N-diglycidylaniline, N,N,O-triglycidyl-p-aminophenol, triglycidyl isocyanurate or N,N,N',N'-tetraglycidyl-bis(p-aminophenyl)methane, hydantoin epoxy resins or aracid epoxy resins or di- or polyglycidyl compounds of polyhydric aliphatic alcohols, such as 1,4-butanediol, trimethylolpropane or polyalkylene glycols. Oxazoli-dinone-modified epoxy resins are also suitable.

Compounds of this type are already known (see: "Angew. Makromol. Chem.", Vol. 44 (1975), pp. 151–163, and US-A 3 334 110); the reaction product of bisphenol A diglycidyl ether with diphenylmethane diisocyanate (in the presence of a suitable accelerator) may be mentioned as an example. In the production of the novel coating composition, the polyepoxide resins can be present individually or in a mixture.

The term "curing" as used herein denotes the conversion of the soluble, fusible polyepoxides to solid, insoluble and infusible, three-dimensionally crosslinked products, generally with simultaneous shaping to give, for example, coatings, impregnated structures and adhesive bonds.

Curing agents can be, for example, aliphatic, cycloaliphatic, aromatic or heterocyclic amines, such as bis(4-aminophenyl)methane, aniline-formaldehyde resins, bis(4-aminophenyl)sulfone, ethylenediamine, propane-1,3-diamine, hexamethylenediamine, diethylenetriamine, triethylenetetramine, 2,2,4-trimethylhexane-1,6-diamine, m-xylylenediamine, bis(4-aminocyclohexyl)methane, 2,2-bis(4-aminocyclohexyl)propane, 3-aminomethyl-3,5,5-trimethylcyclohexylamine (isophoronediamine), polyamidoamines, polyphenols, such as hydroquinone, resorcinol, 2,2-bis(4-hydroxyphenyl)propane (bisphenol A) or phenolaldehyde resins, polycarboxylic acids or their anhydrides, for example phthalic anhydride, tetrahydrophthalic anhydride, hexahydrophthalic anhydride or pyromellitic anhydride. Furthermore, catalytic curing agents, such as cyanoguanidines, or Friedel-Crafts catalysts, such as boron trifluoride, can also be used.

Where amines are used as curing agents, they are normally employed in an amount of from 0.75 to 1.25 equivalents per epoxide equivalent. In the case of polycarboxylic acids or their anhydrides, from 0.4 to 1.1 equivalents per epoxide equivalent are used.

Suitable accelerators are principally imidazole derivatives, for example 2-methylimidazole, 2-phenylimidazole and 2-heptadecylimidazole; also suitable are phosphines, metal soaps and acetylacetonates.

Examples of suitable reactive diluents are mono- or polyhydric alcohols of low molecular weight, which are reacted with epichlorohydrin.

Variation of the ratio of equivalents of polyepoxide compound and diphosphinic acid of formula I allows the phosphorus content of the product to be adjusted. The ratio of equivalents is preferably between 1:0.1 and 1:0.8 and particularly preferably between 1:0.1 and 1:0.4. Reaction of the epoxy resin with a phosphorus-containing dicarboxylic acid or with a phosphorus-containing carboxylic acid anhydride gives a fusible and/or soluble, phosphorus-modified epoxy resin which has a good shelf-life, if desired also in solution, and is easy to handle. In the second reaction step, this is then converted, using a suitable curing agent, into the flame-resistant epoxy resin mixture.

The flame-resistant epoxy resin mixtures are preferably reinforced with glass cloth or glass fibers. They may also include fillers such as quartz powder or alumina trihydrate.

The invention likewise relates to the use of the novel flame-resistant epoxy resin mixtures, or of mixtures produced by the novel process, in coating materials.

The invention also relates to prepregs and composite materials based on inorganic or organic reinforcing materials in the form of fibers, webs or fabrics and produced from the novel epoxy resin mixtures.

Finally, the invention also relates to printed circuit boards made from prepregs produced from glass fiber fabrics together with the novel epoxy resin mixtures.

The invention is described below by means of examples in which a phosphorus compound of formula IV is used:

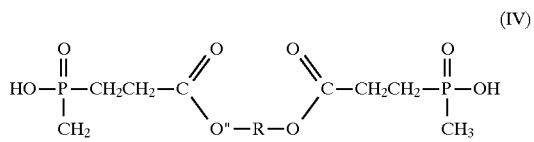

(IV)

EXAMPLE 1

147 g of a bisglycidyl ether of bisphenol A having an epoxide value of 0.55 mol/100 g and 54 g (0.4 mol) of 2-methyl-2,5-dioxo-1,2-oxaphospholane are precharged to a 500 ml five-necked flask fitted with stirrer, dropping funnel, reflux condenser and thermometer, and heated with stirring to 110° C. 12.6 g (0.2 mol) of ethylene glycol are added dropwise at 110° C. during 30 min. Continued stirring for 30 min at 110° C. gives a clear solution. Stirring is continued for a further 2 h at this temperature, and for one hour at 130° C., giving a colorless epoxy resin which is solid at room temperature and has an epoxide value of 0.16 mol/100 g and a phosphorus content of 5.7% by weight.

EXAMPLE 2

147 g of a bisglycidyl ether of bisphenol A having an epoxide value of 0.55 mol/100 g and 54 g (0.4 mol) of 2-methyl-2,5-dioxo-1,2-oxaphospholane in 54 ml of methyl ethyl ketone are precharged to a 500 ml five-necked flask fitted with stirrer, dropping funnel, reflux condenser and thermometer, and heated with stirring to 80° C. 12.6 g (0.2 mol) of ethylene glycol are added dropwise during 30 min. Continued stirring for 30 min gives a clear solution. Stirring is continued for 5 h at 80° C., giving an 80% strength solution of a colorless epoxy resin having an epoxide value of 0.13 mol/100 g and a phosphorus content of 4.6% by weight.

EXAMPLE 3

124 g of a bisglycidyl ether of bisphenol A having an epoxide value of 0.55 mol/100 g and 46 g (0.34 mol) of 2-methyl-2,5-dioxo-1,2-oxaphospholane are precharged to a 500 ml five-necked flask fitted with stirrer, dropping funnel, reflux condenser and thermometer, and heated with stirring to 110° C. 12.9 g (0.17 mol) of 1,3-propanediol are added dropwise at 110° C. during 30 min. Continued stirring for 30 min at 110° C. gives a clear solution. Stirring is continued for a further 2 h at this temperature, and for one hour at 130° C., giving a colorless epoxy resin which is solid at ambient temperature and has an epoxide value of 0.19 mol/100 g and a phosphorus content of 5.8% by weight.

EXAMPLE 4

123 g of a bisglycidyl ether of bisphenol A having an epoxide value of 0.55 mol/100 g and 45 g (0.34 mol) of 2-methyl-2,5-dioxo-1,2-oxaphospholane are precharged to a 500 ml five-necked flask fitted with stirrer, dropping funnel, reflux condenser and thermometer, and heated with stirring to 110° C. 18 g (0.17 mol) of diethylene glycol are added dropwise at 110° C. during 30 min. Continued stirring for 30 min at 110° C. gives a clear solution. Stirring is continued for a further 2 h at this temperature, and for one hour at 130° C., giving a colorless epoxy resin which is solid at ambient temperature and has an epoxide value of 0.21 mol/100 g and a phosphorus content of 5.6% by weight.

EXAMPLE 5

102 g of a bisglycidyl ether of bisphenol A having an epoxide value of 0.55 mol/100 g and 38 g (0.28 mol) of 2-methyl-2,5-dioxo-1,2-oxaphospholane are precharged to a 500 ml five-necked flask fitted with stirrer, dropping funnel, reflux condenser and thermometer, and heated with stirring to 110° C. Then, 15.5 g (0.14 mol) of hydroquinone are added. Continued stirring for 30 min at 110° C. gives a clear solution. Stirring is continued for a further 2 h at this temperature, and for one hour at 130° C., giving a colorless epoxy resin which is solid at ambient temperature and has an epoxide value of 0.21 mol/100 g and a phosphorus content of 5.6% by weight.

EXAMPLE 6

102 g of a bisglycidyl ether of bisphenol A having an epoxide value of 0.55 mol/100 g and 38 g (0.28 mol) of 2-methyl-2,5-dioxo-1,2-oxaphospholane are precharged to a 500 ml five-necked flask fitted with stirrer, dropping funnel, reflux condenser and thermometer, and heated with stirring to 110° C. Then, 15.5 g (0.14 mol) of resorcinol are added. Continued stirring for 30 min at 110° C. gives a clear solution. Stirring is continued for a further 2 h at this temperature, and for one hour at 130° C., giving a colorless epoxy resin which is solid at ambient temperature and has an epoxide value of 0.19 mol/100 g and a phosphorus content of 5.6% by weight.

EXAMPLE 7

100 g of phosphorus-modified epoxy resin of Example 1 are melted at 120° C. and intensively mixed with 3.1 g of micronized dicyandiamide (®Dyhard 100 SF, SKW Trostberg AG) and 0.3 g of imidazole accelerator (®Dyhard MI, SKW Trostberg AG), and cured in a 200×200×2 mm Teflon mold in a for cabinet at 150–180° C. for 4 h. Test specimens of length 127 mm and width 12.7 mm were cut from this molded material.

EXAMPLE 8

100 g of phosphorus-modified epoxy resin of Example 2 are melted at 120° C. and intensively mixed with 22 g of methylcyclohexanedicarboxylic anhydride and 0.4 g of benzyldimethylamine, and cured in a 200×200×2 mm Teflon mold in a drying cabinet at 120–180° C. for 4 h. Test specimens of length 127 mm and width 12.7 mm were cut from this molded material.

EXAMPLE 9

120 g of phosphorus-modified epoxy resin of Example 6 are melted at 120° C. and intensively mixed with 3.3 g of micronized dicyandiamide (®Dyhard 100 SF, SKW Trostberg AG) and 0.3 g of imidazole accelerator (®Dyhard MI, SKW Trostberg AG), and cured in a 200×200×2 mm Teflon mold in a drying cabinet at 150°–180° C. for 4 h. Test specimens of length 127 mm and width 12.7 mm were cut from this molded material.

EXAMPLE 10

100 g of phosphorus-modified epoxy resin of Example 7 are melted at 120° C. and intensively mixed with 25 g of methylcyclohexanedicarboxylic anhydride and 0.4 g of benzyldimethylamine, and cured in a 200×200×2 mm Teflon mold in a drying cabinet at 120°–180° C. for 4 h. Test specimens of length 127 mm and width 12.7 mm were cut from this molded material.

EXAMPLE 11 (comparative example)

150 g of a bisglycidyl ether of bisphenol A (®Beckopox EP 140) having an epoxide value of 0.53 mol/100 g are intensively mixed with 6.9 g of micronized dicyandiamide (®Dyhard 100 SF, SKW Trostberg AG) and 0.3 g of imidazole accelerator (®Dyhard MI, methylimidazole, SKW Trostberg AG), and cured in a 200×200×2 mm Teflon mold in a drying cabinet at 150°–180° C. for 4 h. Test specimens of length 127 mm and width 12.7 mm were cut from this molded material.

Flammability testing was carried out according to the Underwriters Laboratories specification "Test for Flammability of Plastic Materials—UL 94" (02.05.1975 version) on test specimens of 127 mm length, 12.7 mm width and 2 mm thickness. The oxygen index was determined in an apparatus according to ASTM-D 2863-74.

TABLE 1 shows the results of the oxygen index measurements and the flammability tests according to UL 94.

| Epoxy resin molding | Oxygen index | Afterflame time | UL 94 classification |
|---|---|---|---|
| Example 7 | 30.2 | <1', <1' | V-0 |
| Example 8 | 29.4 | <1', <1' | V-0 |
| Example 9 | 29.5 | <1', <2' | V-0 |
| Example 10 | 26.5 | <1', <2' | V-0 |
| Example 11 (comparative example) | 20.5 | burnt | not classified |

The following Examples 12 to 19 show further embodiments of the novel processes.

EXAMPLE 12

134.1 g (1 mol) of oxaphospholane and 55 g (0.5 mol) of resorcinol are mixed and heated to 120° C., giving a clear solution having an acid number of 578 mg KOH/g. After stirring at 140° C. for 1 h, the acid number reduces to 472 mg KOH/g, and after stirring for a further 2.5 h at 140° C., the acid number is reduced as far as 350 mg KOH/g. The product is poured out, cooled and ground.

EXAMPLE 13

42.7 g of product from Example 13 and 150 g of a bisphenol A bisglycidyl ether having an epoxide value of 0.55 mol/100 g are mixed and heated to 130° C. The acid number of the mixture is 80 mg KOH/g. After stirring for 15 min at 130° C., the acid number is 20 mg KOF/g, and the reaction is stopped after 2 h, when the acid number is 4 mg KOH/g, giving a colorless epoxy resin which is solid at room temperature and has an epoxide value of 0.29 mol/100 g and a phosphorus content of 3.5%.

EXAMPLE 14

26.8 g (0.2 mol) of oxaphospholane, 10 g (0.1 mol) of resorcinol and 140 g of a bisphenol A bisglycidyl ether having an epoxide value of 0.55 mol/100 g are mixed and heated to 130° C. The initial acid number of the mixture is 127 mg KOH/g. After stirring for 60 min at 100° C., the acid number is 68 mg KOH/g, and the reaction is stopped after 4 h, when the acid number is 9 mg KOH/g, giving a colorless epoxy resin which is solid at room temperature, and has an epoxide value of 0.31 mol/100 g and a phosphorus content of 3.5%.

EXAMPLE 15

134.1 g (1 mol) of oxaphospholane and 55 g (0.5 mol) of hydroquinone are mixed and heated to 150° C. After stirring at 150° C. for 2 h, the acid number reduces to 355 mg KOH/g, and after stirring for a further 2.5 h at 150° C., the acid number is 350 mg KOH/g. The product is poured out, cooled and ground.

EXAMPLE 16

42.7 g of product from Example 15 and 150 g of a bisphenol A bisglycidyl ether having an epoxide value of 0.55 mol/100 g are mixed and heated to 130° C. After a reaction time of 2 h, a homogeneous melt is obtained, and after a further 4 h of reaction time at 140°–180° C. an acid number is no longer measurable. This gives a colorless epoxy resin which is solid at room temperature and has an epoxide value of 0.15 mol/100 g and a phosphorus content of 3.5%.

EXAMPLE 17

26.8 g (0.2 mol) of oxaphospholane, 10 g (0.1 mol) of hydroquinone and 140 g of a bisphenol A bisglycidyl ether having an epoxide value of 0.55 mol/100 g are mixed and heated to 130° C. The initial acid number of the mixture is 127 mg KOH/g. After stirring for 60 min at 100° C., the acid number is 70 mg KOH/g, after 2.5 h it is 25 mg KOH/g, and the reaction is stopped after 4 h, when the acid number is 5 mg KOH/g. This gives a colorless epoxy resin which is solid at room temperature and has an epoxide value of 0.12 mol/100 g and a phosphorus content of 3.5%.

EXAMPLE 18

899.7 g (6.7 mol) of oxaphospholane and 208.3 g (3.355 mol) of ethylene glycol are mixed. The temperature of the mixture rises to 50°–60° C. After stirring for a further 2 h at 100° C., a light yellow product is formed, which solidifies at about 50° C. The acid number is 340 mg KOH/g.

EXAMPLE 19

50 g of product from Example 18 and 220 g of a bisphenol A bisglycidyl ether having an epoxide value of 0.55 mol/100 g are mixed and heated to 130° C. After a reaction time of 2 h, a homogeneous melt is obtained, and after a further 2 h of reaction time at 140° C. an acid number is no longer measurable. This gives a colorless epoxy resin which is solid at room temperature and has an epoxide value of 0.2 mol/100 g and a phosphorus content of 3.5%.

I claim:

1. A method of using an epoxy resin mixture comprising incorporating said mixture into a coating and applying said coating to electrical or electronic components, wherein said mixture comprises epoxy resin, phosphorous-containing compounds and a curing agent, and wherein said epoxy resin mixture comprises structural units of the formula (I)

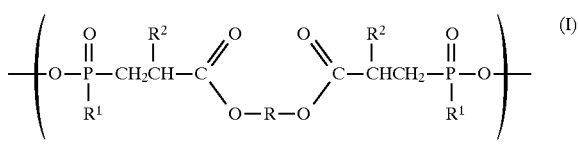

in which R1 is an alkyl or aryl group having from 1 to 10 carbon atoms, R2 is hydrogen or an alkyl group having from 1 to 4 carbon atoms and R is an alkylene, cycloalkylene or arylene group having from 2 to 20 carbon atoms.

2. A prepreg or a composite material based on inorganic or organic reinforcing materials in the form of fibers, webs or fabrics and produced from an epoxy resin mixture wherein said mixture comprises epoxy resin, phosphorous-containing compounds and a curing agent, wherein said epoxy resin mixture comprises structural units of the formula (I)

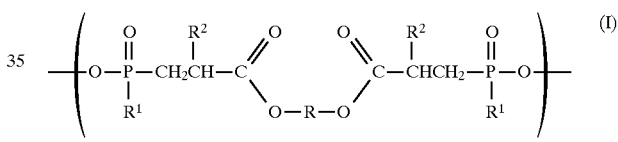

in which R1 is an alkyl or aryl group having from 1 to 10 carbon atoms, R2 is hydrogen or an alkyl group having from 1 to 4 carbon atoms and R is an alkylene, cycloalkylene or arylene group having from 2 to 20 carbon atoms.

3. A printed circuit board made from a prepreg produced from glass-fiber fabrics and an epoxy resin mixture wherein said mixture comprises epoxy resin, phosphorous-containing compounds and a curing agent, wherein said epoxy resin mixture comprises structural units of the formula (I)

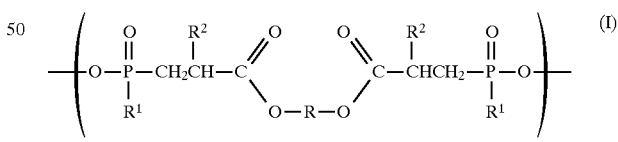

in which R1 is an alkyl or aryl group having from 1 to 10 carbon atoms, R2 is hydrogen or an alkyl group having from 1 to 4 carbon atoms and R is an alkylene, cycloalkylene or arylene group having from 2 to 20 carbon atoms.

* * * * *